(12) United States Patent
Moreno Bermudez et al.

(10) Patent No.: US 9,790,573 B2
(45) Date of Patent: Oct. 17, 2017

(54) METHOD FOR PURIFICATION OF 225AC FROM IRRADIATED 226RA-TARGETS

(71) Applicant: Actinium Pharmaceuticals Inc., New York, NY (US)

(72) Inventors: Josue Manuel Moreno Bermudez, Ismaning (DE); Andreas Turler, Ostermudigen (CH); Richard Henkelmann, Freising (DE); Eva Kabai, Eching (DE); Ernst Huenges, Garching (DE)

(73) Assignee: ACTINIUM PHARMACEUTICALS INC., New York, NY (US)

( * ) Notice: Subject to any disclaimer, the term of this patent is extended or adjusted under 35 U.S.C. 154(b) by 0 days.

(21) Appl. No.: 15/359,053

(22) Filed: Nov. 22, 2016

(65) Prior Publication Data

US 2017/0137916 A1    May 18, 2017

Related U.S. Application Data

(63) Continuation of application No. 14/231,354, filed on Mar. 31, 2014, now Pat. No. 9,534,277, which is a continuation of application No. 13/893,056, filed on May 13, 2013, now abandoned, which is a continuation of application No. 12/280,079, filed as application No. PCT/EP2007/001424 on Feb. 19, 2007, now abandoned.

(30) Foreign Application Priority Data

Feb. 21, 2006 (DE) .................. 10 2006 008 023

(51) Int. Cl.
*A61K 51/00* (2006.01)
*A61M 36/14* (2006.01)
*C22B 60/02* (2006.01)
*C22B 7/00* (2006.01)
*B01D 15/20* (2006.01)
*G21G 1/00* (2006.01)

(52) U.S. Cl.
CPC ........ *C22B 60/0295* (2013.01); *B01D 15/206* (2013.01); *C22B 7/007* (2013.01); *C22B 7/009* (2013.01); *G21G 1/001* (2013.01); *A61K 51/00* (2013.01); *G21G 2001/0089* (2013.01)

(58) Field of Classification Search
None
See application file for complete search history.

(56) References Cited

U.S. PATENT DOCUMENTS

| | | |
|---|---|---|
| 2,442,617 A | 6/1948 | Rosenblum |
| 2,554,649 A | 5/1951 | Tompkins |
| 2,632,763 A | 3/1953 | Hagemann |
| 3,351,049 A | 11/1967 | Donald |
| 3,750,653 A | 8/1973 | Simon |
| 4,293,617 A | 10/1981 | Nagy |
| 4,454,106 A | 6/1984 | Gansow et al. |
| 4,514,266 A | 4/1985 | Cole et al. |
| 4,548,790 A | 10/1985 | Horwitz et al. |
| 4,663,129 A | 5/1987 | Atcher et al. |
| 4,895,633 A | 1/1990 | Seto et al. |
| 5,002,885 A | 3/1991 | Stavrianopoulos |
| 5,085,834 A | 2/1992 | Lemaire et al. |
| 5,246,691 A * | 9/1993 | Geerlings .......... A61K 51/1093 424/1.49 |
| 5,355,394 A | 10/1994 | van Geel et al. |
| 5,445,720 A | 8/1995 | Sypula et al. |
| 5,607,591 A | 3/1997 | Dozol et al. |
| 5,707,528 A | 1/1998 | Berry |
| 5,809,394 A | 9/1998 | Bray et al. |
| 5,863,439 A | 1/1999 | Dietz et al. |
| 5,885,465 A | 3/1999 | Bray et al. |
| 6,092,889 A | 7/2000 | Nakamoto et al. |
| 6,299,666 B1 | 10/2001 | Apostolidis et al. |
| 6,461,433 B1 | 10/2002 | Carden, Jr. et al. |
| 6,511,603 B1 | 1/2003 | Dietz et al. |

(Continued)

FOREIGN PATENT DOCUMENTS

DE      103 47 459 B3    5/2005
DE  10 2005 043 012.0    9/2005

(Continued)

OTHER PUBLICATIONS

Apostolidis et al. (Appl. Radiat. Isot. 2005, 62, 383-387).*
Vreček et al. (Appl. Radiat. Isot. 2004, 60, 717-723).*
Johnson et al. (Nuclear Instruments and Methods in Physics Research A 1998, 414, 459-465).*
Apostolidis et al., 2005, "Cyclotron Production of Ac-225 for Targeted Alpha Therapy", Applied Radiation Isotopes, 62:383-387.
Burnett, W.C. et al., "Determination of Radium-228 in Natural Waters Using Extraction Chromatographic Resins," Radioactivity and Radiochemistry, 6(3): p. 2-25 (Sep. 1995).
Chabaux, F. et al., "A new Ra—Ba chromatographic separation and its application to Ra mass-spectrometric measurement in volcanic rocks," Chemical Geology 114 (1994) 191-197.
Chiarizia, R. et al. "Uptake of Metal Ions by a New Chelating Ion-Exchange Resin. VII. Alkaline Earth Cations" Solvent Extraction and Ion Exchange, 13(6): 1063-1082 (1995).
Geerlings et al., "The feasibility of 225Ac as a source of α-particles in radioimmunotherapy," Nuclear Medicine Communications 14: 121-125 (1993).
Geerlings, M.W. "Radionuclides for radioimmunotherapy: criteria for selection," The International Journal Biological Markers, vol. 8, No. 3; pp. 180-186 (1993).

(Continued)

*Primary Examiner* — Michael G Hartley
*Assistant Examiner* — Melissa Perreira
(74) *Attorney, Agent, or Firm* — Wilmer Cutler Pickering Hale and Dorr LLP

(57) ABSTRACT

The present invention describes a method for purification of $^{225}$Ac from irradiated $^{226}$Ra-targets provided on a support comprising a leaching treatment of the $^{225}$Ra-targets for leaching essentially for the entirety of $^{223}$Ac and $^{226}$Ra with nitric or hydrochloric acid, followed by a first extraction chromatography for separating $^{225}$Ac from $^{226}$Ra and other Ra-isotopes and a second extraction chromatography for separating $^{225}$Ac from $^{210}$Po and $^{210}$Pb. The finally purified $^{225}$Ac can be used to prepare compositions useful for pharmaceutical purposes.

22 Claims, 5 Drawing Sheets

(56) References Cited

U.S. PATENT DOCUMENTS

| | | | |
|---|---|---|---|
| 6,635,234 B1 * | 10/2003 | Larsen | A61K 51/1282 424/1.11 |
| 6,676,987 B2 | 1/2004 | Zhong et al. | |
| 7,106,438 B2 | 9/2006 | Morrisroe et al. | |
| 7,378,372 B2 | 5/2008 | Sylvester | |
| 8,153,087 B2 | 4/2012 | Kabai et al. | |
| 8,349,391 B2 | 1/2013 | Harfensteller et al. | |
| 8,715,598 B2 | 5/2014 | Kabai et al. | |
| 2003/0127395 A1 | 7/2003 | Bond et al. | |
| 2003/0194364 A1 * | 10/2003 | Bond | G21G 1/0005 423/2 |
| 2003/0219366 A1 * | 11/2003 | Horwitz | G21G 4/08 423/2 |
| 2005/0211955 A1 | 9/2005 | Meikrantz et al. | |
| 2007/0076834 A1 | 4/2007 | Moreno Bermudez et al. | |
| 2007/0153954 A1 | 7/2007 | Harfensteller et al. | |
| 2009/0191122 A1 | 7/2009 | Moreno Bermudez et al. | |
| 2010/0104489 A1 | 4/2010 | Kabai et al. | |

FOREIGN PATENT DOCUMENTS

| | | | |
|---|---|---|---|
| DE | 10 2004 022 200 A1 | 12/2005 | |
| DE | 10 2006 042 191 A1 | 7/2007 | |
| DE | 10 2006 008 023 A1 | 8/2007 | |
| EP | 0 443 479 B1 | 7/1994 | |
| EP | 0752709 A1 | 1/1997 | |
| EP | 0752710 A1 | 1/1997 | |
| EP | 0 752 709 B1 | 3/1999 | |
| EP | 0 752 710 B1 | 11/1999 | |
| EP | 0 962 942 A1 | 12/1999 | |
| EP | 1 673 492 B1 | 3/2009 | |
| EP | 2082071 A1 | 7/2009 | |
| JP | 04326096 A | 11/1992 | |
| JP | 2002-517005 | 6/2002 | |
| JP | 2010-502965 | 1/2010 | |
| LU | EP 0962942 A1 * | 12/1999 | G21G 1/10 |
| WO | WO-98/55201 | 12/1998 | |
| WO | WO-99/62073 A1 | 12/1999 | |
| WO | WO-99/63550 A1 | 12/1999 | |
| WO | WO-2005/039634 | 5/2005 | |
| WO | WO-2005/039647 A2 | 5/2005 | |
| WO | WO-2005/105160 | 11/2005 | |
| WO | WO-2007/096119 | 8/2007 | |
| WO | WO-2008/028664 | 3/2008 | |

OTHER PUBLICATIONS

Gerlach, V.W. et al. "Zeitschrift fur anorganische und allgemeine Chemie" Band 221 (1934), 103-108 (with English Summary).
Gleason, et al., 1980, "An Improved Ion Exchange Procedure for the Separation of Barium from Radium," Ann Arbor Science Publishers Inc., p. 47-50.
Haissinsky, M.J., "Electrolyse de sels de baryum st de radium dans l'acetone," ("Electrolysis of salts of barium and radium in acetone") Chim. Phys. (1937) 34, 323-325 (with English translation of summary).
Hassfjell et al., "The Development of the α-Particle Emitting Radionuclides 212Bi and 213Bi, and Their Decay Chain Related Radionuclides, for Therapeutic Applications," Chem. Rev., 101: 2019-2036 (2001).
Honigschmid, V.O. et al., "Zeitschrift fur anorganische und allgemeine Chemie," Band 221 (1934), 65-82 (with English Summary).
Huber et al., "Locoregional α-Radioimmunotherapy of Intraperitoneal Tumor Cell Dissemination Using a Tumor-specific Monoclonal Antibody," Clinical Cancer Research (Suppl.) 9:1s-6s (2003).
Huber, Roswitha, "Bewertung der lokoregionalen Radioimmuntherapie disseminierter Tumorzellen des diffusen Magenkarzinoms mit einem 213Bi gekoppelten tumorspezifischen Antikörper im Mausmodell" (Evaluation of a locoregional radioimmunotherapy of disseminated tumor cells of the diffuse gastric carcinoma with a 213Bi bound tumor specific antibody in the mouse model), doctorate dissertation in the Faculty of Veterinary Medicine submitted to the Ludwig-Maximilians-University of Munich, Jul. 18, 2003 (English Summary—pp. 108-109).
Ingelbrecht, C., et al.: "Improved electrodeposited actinide layers," Nuclear Instruments and Methods in Physics Research, A 397 (1997) 34-38.
International Search Report and Written Opinion of International Patent Application No. PCT/EP2004/011510, filed Oct. 13, 2004.
International Search Report and Written Opinion of International Patent Application No. PCT/EP2005/002619 filed Mar. 11, 2005.
International Search Report and Written Opinion, International Patent Application No. PCT/EP2007/007788 mailed Dec. 17, 2007.
International Search Report and Written Opinion, International Patent Application No. PCT/EP2007/01424 mailed Aug. 22, 2007.
Johnson et al., 1998, "A 222Rn Source for Low-Background Liquid Scintillation Detectors", Nuclear Instruments and Methods in Physics Research A 414 (1998) 459-465.
Jurcic et al., "Target α particle immunotherapy for myeloid leukemia," Blood, Aug. 15, 2002, vol. 100, pp. 1233-1239.
Kabai, E. "Radium purification for cyclotron target preparation for $^{225}$Ac Production": Sep. 11 to Sep. 14, 2005 Dusseldorf, Techische Universitat Munchen, Institut fur Radiochemie, 1-19.
Kabai, E. et al., "Simultaneous determination of radioactive halogen isotopes and $^{99}$Tc," Czechoslovak Journal of Physics, vol. 53, Suppl. A., A181-A188 (2003).
Kaspersen, et al., "Cytotoxicity of 213Bi- and 225Ac-immunoconjugates," Nuclear Medicine Communications, 16:468-476 (1995).
Kirby, H.W. et al., "The Radiochemistry of Radium," National Academy of Sciences, National Research Council, Nuclear Science Series, Issued Dec. 1964.
Mirzadeh, S., "Generator-produced Alpha-emitters," Appl. Radiat. Isot., vol. 49, No. 4, pp. 345-349, 1998.
Moon, D.S. et al., "Preconcentration of radium isotopes from natural waters using $MnO_2$ Resin," Applied Radiation and Isotopes 59: 255-262 (2003).
Mullen, G. et al., "Preparation of Targets of Np, Pu, Am, Cm and Cf by Electrodeposition from Organic Solutions," Nuclear Instruments and Methods 128 (1975) 425-428.
Nelson, F. "Ion Exchange Procedures V. Separation of Barium and Radium," Journal of Chromatography, 16: 403-406 (1964).
Nikula et al., "Alpha-Emitting Bismuth Cyclohexylbenzyl DTPA Constructs of Recombinant Humanized Anti-CD33 Antibodies: Pharmacokinetics, Bioactivity, Toxicity and Chemistry," The Journal of Nuclear Medicine, vol. 40, No. 1, Jan. 1999, 166-176.
Power, W.H. et al. "Separation of Radium and Barium by Ion Exchange Elution," Analytical Chemistry, 31(6):1077-1079 (1959).
Rompp Lexikon Chemie 10th Edition, 1997, pp. 1965-1966.
Salutsky, M.L. et al., "Radium-Barium Separation Process," Industrial and Engineering Chemistry, Oct. 1955, pp. 2162-2166.
Schicha and Schober, 1997 "Nuklearmedizin—CompactLehrbuch," section 2.3.1, pp. 15, Schattauer Gmbh.
Schicha and Schober, 2003 "Nuklearmedizin—Basiswissen und klinische Anwendung," Section 2.3.1, pp. 13-14, Schattauer Gmbh.
Strelow, F.W.E. "Separation of Traces and Large Amounts of Lead from Gram Amounts of Bismuth, Tin, Cadmium, and Indium by Cation Exchange Chromatography in Hydrochloric Acit-Methanol Using a Macroporous Resin," Analytical Chemistry, vol. 57, No. 12, Oct. 1985, pp. 2268-2271.
Tompkins, E.R. "Separation of Radium from Barium by the Use of an Ion-exchange Column Procedure," J. Am. Chem. Soc. 70 (10): 3520-2 (1948).
van der Walt, T.N. et al., "Quantitative Separation of Gallium from other Elements by Cation-Exchange Chromatography," Anal. Chem., 55: 212 (1983).
Vrecek et al., "Determination of 210Pb and 210Po in Sediment and Soil Leachates and in Biological Materials Using a Sr-Resin Column and Evaluation of Column Reuse," Applied Radiation and Isotopes 60 (2004) 717-723.
Wang, S. et al., "Nuclear Data for Production of Therapeutic Radionuclides," Nuclear Physics Review, vol. 23, No. 1, Mar. 2006, pp. 78-83 (with English translation of abstract).

(56) References Cited

OTHER PUBLICATIONS

Whitehead, N.E., et al.: "Factors Affecting the Electrodeposition of $^{226}$Ra," Journal of Radioanalytical and Nuclear Chemistry, Articles, vol. 160, No. 2 (1992) 447-485.

Wlodzimirska, B. et al. "Preparation of $^{225}$Ac and $^{228}$Ac generators using a cryptomelane manganese dioxide sorbent," Radiochimica Acta, 91:553-556 (2003).

* cited by examiner

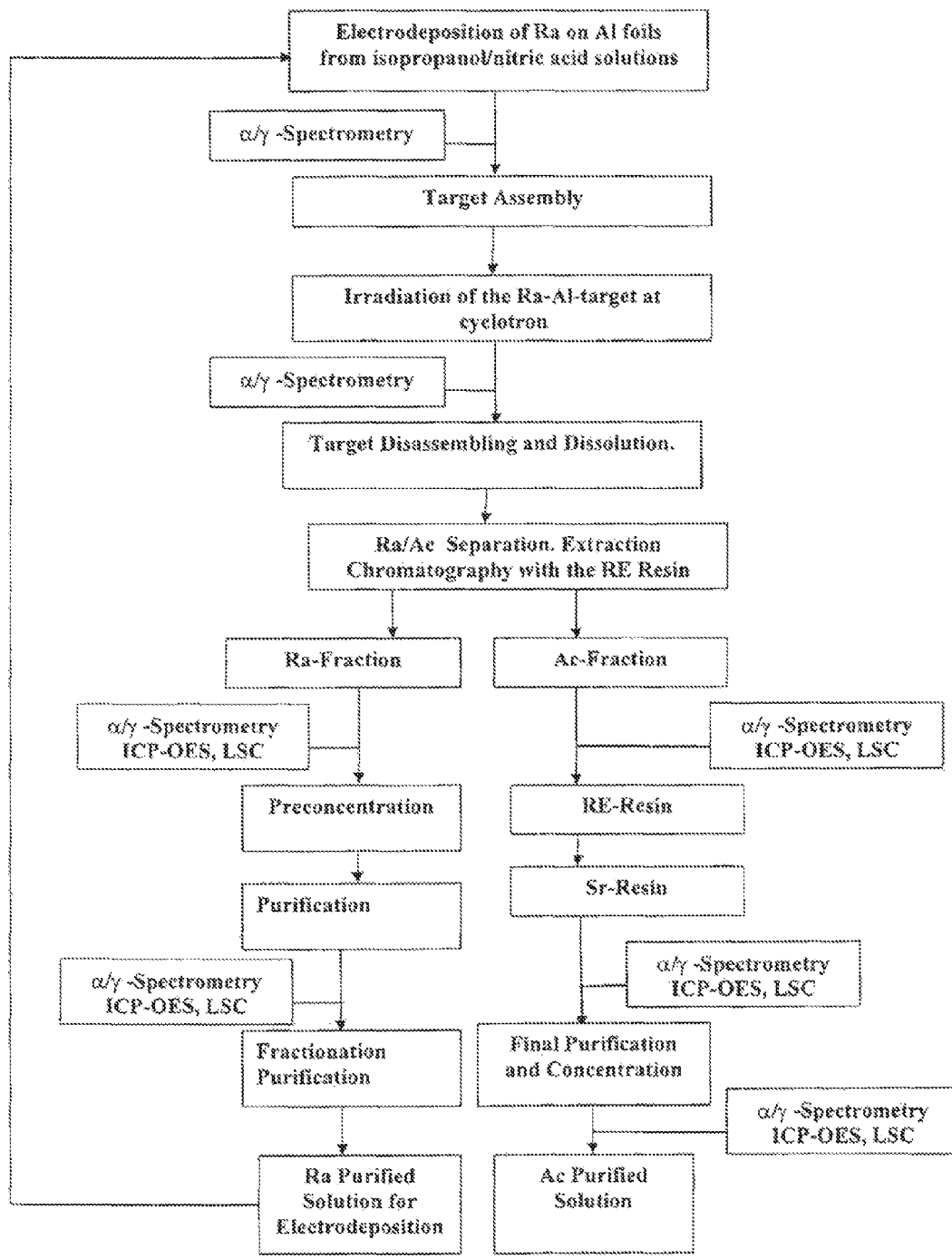
Fig.1. General Scheme for the Extraction of Ac from Ra/Al Irradiated Targets

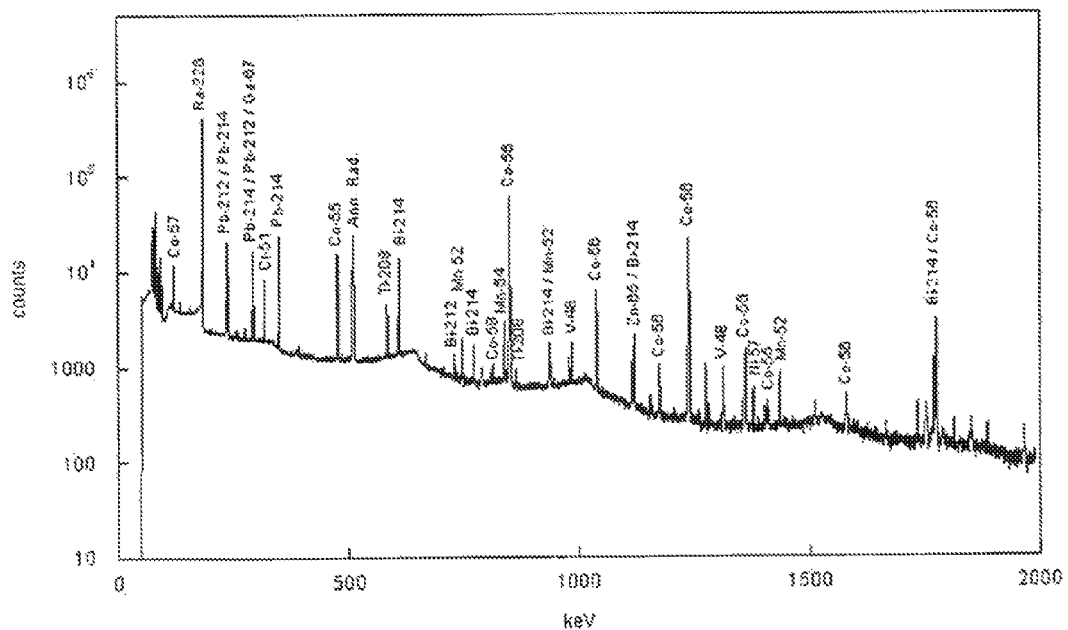
Fig. 2a: γ-spectrum of the ²²⁵Ra-fraction after the first Ra/Ac separation with RE Resin

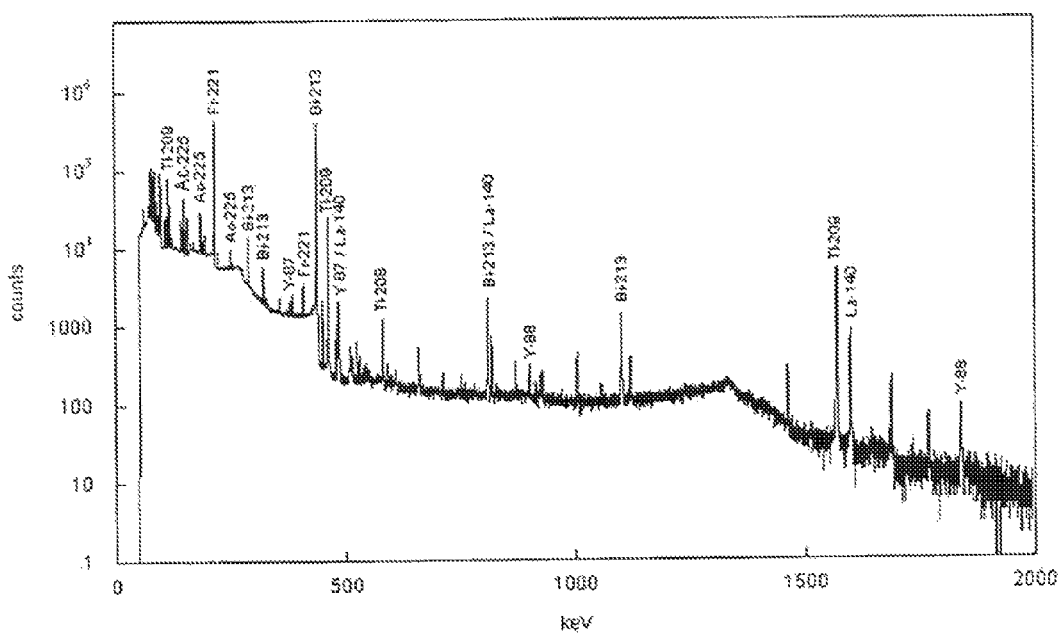
Fig. 2b: γ-spectrum of the purified 225Ac-fraction

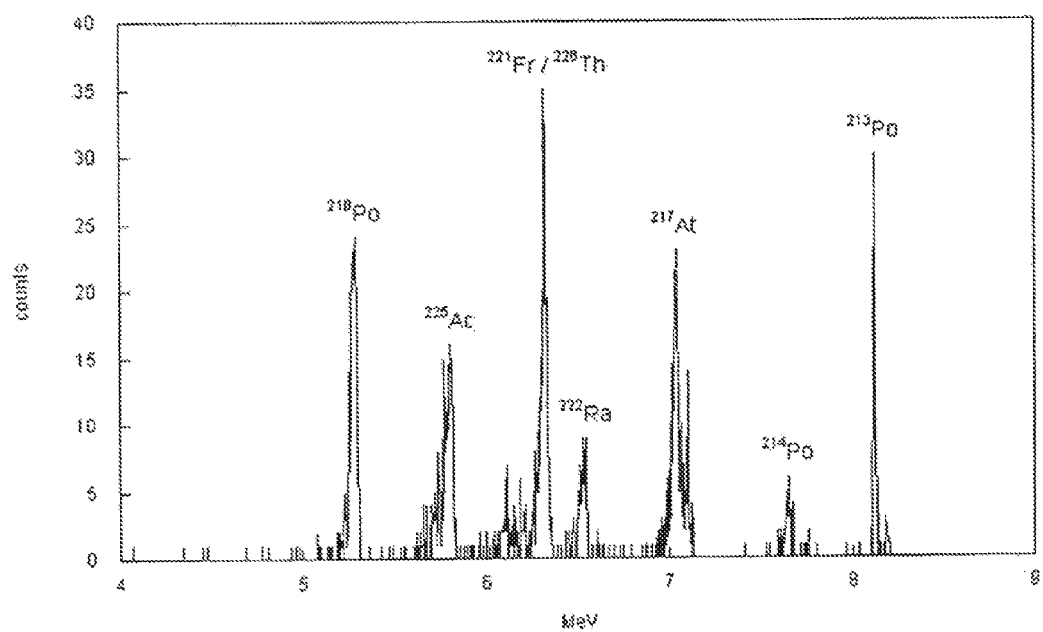
Fig.3a: α-spectrum of 225Ac before Po and Pb purification

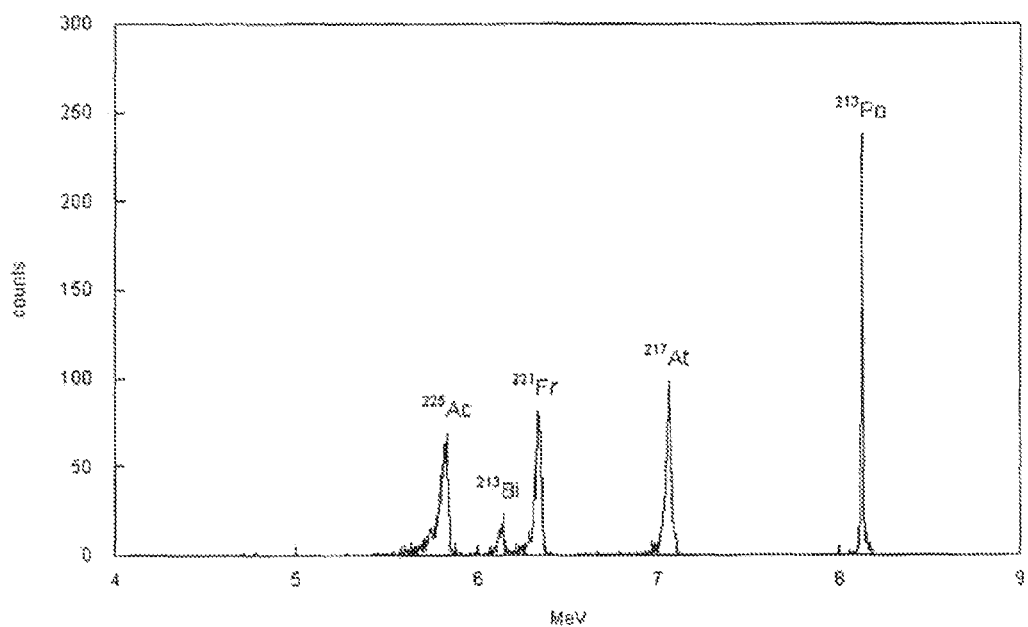
Fig. 3b: α-spectrum of ²²⁵Ac after Po and Pb purification

METHOD FOR PURIFICATION OF 225AC FROM IRRADIATED 226RA-TARGETS

This application is a Continuation of U.S. patent application Ser. No. 14/231,354 filed Mar. 31, 2014, which is a Continuation of U.S. patent application Ser. No. 13/893,056 filed May 13, 2013, which is a Continuation of U.S. patent application Ser. No. 12/280,079 filed Feb. 6, 2009, which is a U.S. National Phase Application under 35 U.S.C. §371 of International Patent Application No. PCT/EP2007/001424, filed Feb. 19, 2007, which claims priority to German Patent Application No. 102006008023.8, filed Feb. 21, 2006, each of which is herein incorporated by reference in its entirety.

The present invention relates to a Method for purification of $^{225}$Ac from irradiated $^{226}$Ra-targets provided on a support according to claims 1 to 3. Furthermore, the invention relates to an $^{225}$Ac-containing radionuclide composition in accordance with claim 21.

In particular, the radionuclide $^{225}$Ac can be successfully used in nuclear medicine—bound to tumorspecific antibodies—in various clinical trials in the treatment of cancer, particularly in form of its daughter nuclide $^{213}$Bi.

Already in 1993, criteria for the selection of radionuclides for immunotherapy with α-emitters and β-emitters were provided for the first time (GEERLINGS, M. W. (1993): Int. J. Biol. Markers, 8, 180-186: "Radionuclides for radioimminunotherapy: criteria for selection") where it turned out due to the difference in energy that the radioactivity of α-emitters to be applied may be more than 1000 times lower than that of β-emitters, if a comparable effect is to be achieved.

Moreover, in the above literature, the α-emitting radionuclides $^{225}$Ac and its daughter isotope $^{213}$Bi turned out to be highly promising for the objects of radioimmunotherapy alongside the in principle usable, however relatively poorly available or instable antibody conjugate producing α-emitters: $^{211}$At, $^{255}$Fm, $^{212}$Bi/$^{212}$Pb, $^{224}$Ra, $^{233}$Ra.

One of the fundamental studies for the foundation of a radioimmunotherapy with αemitters is disclosed in GEERLINGS, M. W., KASPERSEN, F. M., APOSTOLIDIS; C. and VAN DER HOUT, R. (1993): Nuclear Medicine Communications 14, 121-125, "The feasibility $^{225}$Ac as a source of α-particles in radioimmunotherapy". Here it is described that $^{225}$Ac produced from $^{229}$Th and the daughter isotope of $^{225}$Ac, namely $^{213}$Bi is suitable as isotope for the radioimmunotherapy with α-emitters. As indications there are described in particular cancer treatment and the treatment of micrometastases of malign tumors using tumor-specific monoclonal antibodies as carriers for α-emitters.

A further study of KASPERSEN, F. M., BOS, E., DOORNMALEN, A. V., GEERLINGS, M. W., APOSTOLIDIS, C. and MOLINET, R. (1995): Nuclear Medicine Communications, 16, 468-476: "Cytotoxicity of $^{213}$Bi- and $^{225}$Ac-immunoconjugates" confirms and quantifies the cytotoxic effect of $^{213}$Bi and $^{225}$Ac with in vitro tests using the human epidermoid tumor cell line A431.

Moreover, it is suggested to use $^{213}$Bi for the treatment of malignant diseases of the blood system.

Further, in KASPERSEN et al. 1995 a process can be found with which antibodies can be bound chemically to a chelator suitable for $^{213}$Bi and $^{225}$Ac. It has proved that for example p-isothiocyanatobenzyl-diethylentriamine-pentaacetate (benzyl-DTPA) is particularly suitable.

Another chelator, namely Cyclohexyl-DTPA is, for example, described in NIKULA, T. K., McDEVITT, M. R., FINN, R. D., WU, C., KOZAK, R.W., GARMESTANI, K., BRECHBIEL, M. W., CURCIO, M. J., PIPPIN, C. G., TIFFANY-JONES, L., GEERLINGS, M. W., Sr., APOSTOLIDIS, C., MOLINET, R., GEERLINGS, M. W., Jr., GANSOW, O. A. UND SCHEINBERG, D. A. (1999): J Nucl Med, 40, 166-176: "Alpha-Emitting Bismuth Cyclohexylbenzyl DTPA Constructs of Recombinant Humanized Anti-CD33 Antibodies: Pharmacokinetics, Bioactivity, Toxicity and Chemistry".

An overview over chelator chemistry can be found for example in HASSFJELL, S, and BRECHBIEL, W. (2001): Chem. Rev., 101, 2019-2036:

"The Development of the α-Particle Emitting Radionuclides $^{212}$Bi and $^{213}$Bi, and Their Decay Chain Related Radionuclides, For Therapeutic Applications"

In the meantime, various radioimmunotherapeutic approaches with $^{225}$Ac and $^{213}$Bi for the treatment of cancer are in various phases of clinical trials.

The medical-clinical significance of the present invention may be seen for example from two promising therapeutic approaches:

On the one hand, JURCIC, J. G., LARSON, S. M., SGOUROS, G., McDEVITT, M. R., FINN, R. D., DIVGI, C. R. Ase, M. B., HAMACHER, K. A., DANGSHE, M., HUMM, J. L., BRECHBIEL, M. W., MOLINET, R., SCHEINBERG, D. A. (2002) in Blood, 100, 1233-1239 report a significant success in the treatment of patients with acute myelogenous leukaemia (AML) and chronic myelogenous leukaemia (CML) by using $^{213}$Bi, which is bound to HuM195, a formulation of a monoclonal anti-CD33-antibody, which was developed for the humane medicine. This study was the first proof-of-concept where a human being was treated with a systemic radioimmunotherapy comprising an α-emitter, which is transported to a tumorspecific cellular target.

On the other hand, HUBER, R., SEIDL, C., SCHMID, E, SEIDENSCHWANG, S., BECKER; K.-F., SCHUMACHER, C., APOSTOLIDIS, C., NIKULA, T., KREMMER, E., SCHWAIGER, M. and SENEKOWITSCE-SCHMIDTKE, R. (2003): Clinical Cancer Research (Suppl.) 9, 1s-6s: "Locoregional α-Radioimmunotherapy of Intraperitoneal Tumor Cell Dissemination Using a Tumorspecific Monoclonal Antibody" report the therapeutic effectivity of $^{213}$Bi-d9MAB—with low bone marrow toxicity—and the possible application of a locoregional therapy for patients who suffer from gastric carcinoma, who express d9-E-Cadherine.

More results of studies and partial aspects in this matter are shown in: Roswitha HUBER, doctorate dissertation in the Faculty of Veterinary Medicine submitted to the Ludwig-Maximilians-University of Munich, Jul. 18, 2003: "Bewertung der lokoregionalen Radioimmuntherapie disseminierter Tumorzellen des diffusen Magenkarzinoms mit einem $^{213}$Bi gekoppelten tumorspezifischen Antikörper inn Mausmodell" (Evaluation of a locoregional radioimmunotherapy of disseminated tumor cells of the diffuse gastric carcinoma with a $^{213}$Bi bound tumor specific antibody in the mouse model).

This dissertation was originated from Nuklearmedizinische Klinik and Poliklinik of the Technical University of Munich, the University hospital "Klinikum rechts der Isar", dean: Prof. Dr. M. Schwaiger. The dissertation was prepared under the supervision of Prof. Dr. med. Dr. phil. Reingard Senekowitsch-Schmidtke and was presented to the veterinary faculty via Prof. Dr. med. vet. K. Tempel, Institute for Pharmacology, Toxicology and Pharmacy of the Faculty of Veterinary Medicine of the Ludwig-Maximillans-University of Munich, director: Prof. Dr. med. vet. R. Schulz.

According to HUBER 2003, each year 18 out of 100 000 Germans come down with gastric carcinoma alone. In Japan, even 126 out of 100 000 people are affected. This means about 156 000 incidences per year in Japan alone. There, as well as in China, Taiwan and Korea, gastric carcinoma is one of the most frequent causes of death in consequence of a tumor. When a peritoneal carcinomatosis, the consequence of diffuse expansion of tumor cells in the abdominal cavity, is diagnosed, the life expectancy of a patient is at present about 12 months. Even with resectable gastric carcinoma, this means with carcinoma, which have not yet disseminated and with negative diagnostic findings with respect to lymph nodes, the relapse-free three-year survival-rate is at about 45%, only.

Up to now the application of cytostatica within a chemotherapy seemed to be the most promising therapeutic way.

However, the side effects range from immunosuppression, coagulopathy, metabolic anoxia, mucositis and hyperuricaemia to the danger of cytostatica induced secondary tumors. Particularly affected is here quickly proliferating tissue as bone marrow and the epithelium of the gastrointestinal tract as well as of the oral mucosa.

The radioimmunotherapy, in contrast, uses protein structures located on the membrane, that are expressed by tumor cell lines in order to bind cytotoxic active substances via a carrier. Mostly, an overexpression of the binding molecule at the tumor cell is central to a radioimmunotherapy. The target molecule for the tumor associated antibodies is thus also expressed to a lower extend in physiologic cells of the organism. This implies that any therapeutic agent for radiotherapy also binds to these cells.

Particularly, in the treatment of acute or chronic myelogenous leukaemia the meaning of the present invention takes effect, namely for the preparation of a suitable α-emitter, namely $^{225}$Ac which forms through decay reaction the bound, for example, to a tumorspecific antibody.

The $^{213}$Bi atom decays via β-decay to $^{213}$Po, which releases its α-decay energy of 8,4 MeV with a half life of 4 μs in the tissue within a distance of 80 μm when decaying and thus kills effectively cells in its immediate neighborhood due to its high linear energy transfer.

The so called locoregional application enables a quick binding of $^{213}$Bi bound tumor specific antibody to the tumor antigenes with maximal therapeutic success and minimal toxicity.

Not before the late 80s was the α-emitting nuclide pair $^{213}$Bi/$^{213}$Po was discovered for radioimmunotherapy. However, in the standard textbook of Schicha and Schober, 1997 "Nuklearmedizin-Basiswissen and klinische Anwendung" (nuclear medicine—basic knowledge and clinical application) it can be read: "The linear energy transfer of α-rays is so big that the likeliness for the creation of irradiation damages is bigger than a therapeutic effect. For this reason, nuclides, which release α-rays, are not applied in the nuclear medicine . . . ", ("Der lineare Energietransfer ist bei α-Strahlen so groβ, daβ die Wahrscheinlichkeit für die Erzeugung von Strahlenschäden größer ist als ein therapeutischer Effekt. Aus diesem Grunde werden Nuklide, die α-Strahlen emittieren, in der Nuklearmedizin . . . nicht eingesetzt.")

However, in the clinical application of such α-emitters in combination with tumorspecific antibodies, exactly the opposite has proved to be true (cf. JURCIC et al. 2002). Consequently, the question arose which isotope it was best to use and how it could be prepared reliably and continuously.

Most of the over hundred available α-emitters can already be excluded from in vivo application for practical reasons (cf. GEERLINGS 1993). These α-emitters have to meet requirements like sufficient chemical and physical purity, economic availability and an adequate half-life. The latter has to be long enough for binding to the antibodies and for the biologic allocation and has to be short enough so that the patient is not put at an unnecessary risk due to excessive exposition to the rays.

One of the few α-emitter which fulfill these criteria is the nuclide pair $^{213}$Bi/$^{213}$Po with a half-life of 45,6 min ($^{213}$Bi). The photon emission of $^{213}$Bi with 440 KeV additionally permits an in vivo scintiscanning of the patient as well as an easy measurement of the activity using an α-ray counter.

Moreover, in radiation protection it is important that the radiation can be detected easily. Furthermore, also traces of further daughter nuclides of $^{225}$Ac/$^{213}$Bi as for example $^{221}$Fr or $^{209}$Pb can be determined by new methods of measurement and can also be included into the dosimetry alongside the quality control.

In the meantime, $^{213}$Bi has become available via the production of $^{225}$Ac, for example according to EP 0 752 709 B1 and EP 0 962 942 A1 and particularly via the so called "thorium cow" according to U.S. Pat. No. 5,355,394. However, the production via the above-mentioned "thorium cow" is very expensive, as it derives from a neutron irradiation of $^{226}$Ra over several years, whereby finally among others an isotope mixture of $^{228}$Th and $^{229}$Th is assembled, whereby $^{229}$Th again decays via $^{225}$Ra into $^{225}$Ac, which decays to $^{213}$Bi.

Thus, the mother-daughter nuclide pair $^{225}$Ac/$^{213}$Bi is available in principle, however, neither in an adequate quantity and continuously nor at an acceptable price, however—as mentioned initially—first clinical studies with $^{225}$Ac/$^{213}$Bi conjugated to HuM195, a humanized anti-CD33 monoclonal antibody are very successful against myeloid leukaemia. The first clinical phase I trials with $^{213}$Bi-HuM195 were carried out with excellent therapeutic results at leukaemia patients at the Memorial Sloan-Kettering Cancer Center in New York (JURICIC et at 2002).

In cyclotrons, developed for the first time 1931, electrically charged particles are moving on spiral shaped orbits in magnetic flux lines.

In particular, protons can be accelerated with the help of a cyclotron with currents that are high enough to such high velocities that they can be used in experimental and applied nuclear physics for the production of isotopes in a quantitative scale.

EP 0 752 709 B1 describes, for example, a method for producing Actinium-225 from Radium-226, whereby accelerated protons are projected in a cyclotron onto a target of radium-226, characterized in that protons accelerated in a cyclotron are projected onto a target of radium-226 in a cyclotron, so that the instable compound nucleus $^{227}$Ac is transformed into Actinium-225 while emitting two neutrons (p,2n-reaction), whereby after a waiting period, during which the Actinium-226, which has been created simultaneously due to the emission of only one neutron, decays mostly due to its considerably shorter half-life and Actinium is chemically separated, so that a relatively pure isotope Ac-225 is obtained.

Nevertheless, the final product contains unconverted $^{226}$Ra and other Ra isotopes. In addition, different decay products of Actinium occur as well as nuclear conversions of contaminating elements of the Al.

Particularly important is to minimize the content of Sr and Ba which lead to the production of radioisotopes of Y and La, respectively.

Several radioisotopes are produced as a result of nuclear reactions type (p,n) or (p,2n) on main impurities like Ba, Fe, Zn, Sr, Pt, V, Ti, Cr and Cu which are present in the Al carrier (foil, mesh) and/or in the Ra deposit. The radionuclides of major contribution to the total gamma activity excluding $^{226}$Ra and daughters are typically the following: $^{135}$La, $^{55}$Co, $^{56}$Co, $^{67}$Ga, $^{57}$Ni, $^{135m}$Ba, $^{133m}$Ba, $^{131}$Ba, $^{129}$Cs, $^{51}$Cr, $^{48}$V, $^{52}$Mn, $^{54}$Mn, $^{65}$Zn.

In addition, disturbing radiochemical impurities are $^{210}$Po and $^{210}$Pb resulting from the following decay chain: Ra-226 (alpha).→Rn-222(alpha) →Po-218 (alpha)→Pb-214 (beta) →Bi-214 (beta)→Po-214 (alpha)→Pb-210 (beta)→Bi-210 (beta)→Po-210 (alpha)→Pb-206 (stable).

The $^{226}$Ra target used according to the procedure of EP 0 752 709 B1 is not specified in detail there.

EP 0 962 942 A1 also describes a method for producing Ac-225 by irradiation of $^{226}$Ra with cyclotron accelerated protons having an energy of 10 to 20 MeV.

According to the prior art of EP 0 962 942 A1, the target nuclide $^{226}$Ra is used in the form of $RaCl_2$, which can be obtained for example by precipitation with concentrated HCl or radiumcarbonate ($RaCO_3$). These radium substances are then pressed into target pellets. Prior to irradiation of the radium salts with protons, the pellets are heated to about 150° C. in order to release crystal water and are then sealed in a silver capsule. The capsule is then mounted on a frame-like support and connected to a water cooling circuit. The target itself exhibits a window, which is arranged in a way that the proton beam hits the target through the window. According to EP 0 962 942 A1, the target exhibits a surface of about 1 cm$^2$.

Although it is already possible to achieve good Actinium-225-yields with the targets according to EP 0 962 942 A1, it has turned out in practice that this target construction can heat itself under certain conditions due to the proton beam in such a way that the silver capsule tears open and might thus both destroy the target and contaminate the peripheral compounds.

In order to solve these target problems, the inventors of the present inventions have designed two different improved radium targets for the production of radionuclides by means of accelerated protons, on the basis of the prior art of EP 0 962 942 A1.

The one target preparation, a method of electrodeposition of $^{226}$Ra-material is disclosed in Applicant's DE 103 47 459 B3, the other one, an evaporation-dispensing system, is disclosed in Applicant's DE 10 2004 022 200 A1. Both application papers are herewith incorporated by reference in their entirety.

Applicant's methods of target preparation provide the finally desired $^{225}$Ac-product on an Aluminium surface, and in a mixture of different radionuclides.

Preferably, Al-mesh targets can be used as carrier of Ra in the targets.

Al-mesh targets have an advantage in the achieved yield during electrodeposition. With the introduction of the Al-mesh disc as cathode in the electrodeposition process and as carrier of Ra in the target, the amount of Ra that can be deposited per disc could be increased. While, e.g. on an Al-foil disc the amount of Ra (experiments conducted at mg levels with Ba and at microgram levels with Ra-226) deposited was below 10 mg (2-3 mm at the eddies of one disc), in the case of the mesh disc, the amount of Ra was to approximately 70 mg (depending on the thickness of the deposit and other parameters, thicker deposits were not well adhered to the mesh anymore). Consequently the number of Ra/Al mesh discs that need to be introduced into the target cup was reduced to five or six instead of 10 or more as it was required by the use of Al-foil discs. The better yield of electrodeposition on Al mesh compared with the yield of Al foil is associated with the higher surface of the mesh. The fact that more Ra is electrodeposited on the Al also assures that the proton beam is hitting with higher probability the Ra and not much loss occurs in Al.

The improvement by using an Al-mesh also facilitated the automation of the process.

Preferably, a 99% pure Al provided by Good Fellow is used. The neutron activation results carried out on the mesh at the institute are reported below:

Impurities in the Al mesh measured by ko-INAA are given in Table 1

TABLE 1

| Element | Content [µg/g] |
|---|---|
| Fe | 1302 |
| Cr | 701 |
| Ni | 0.2 |
| Ga | 145 |
| Zn | 39 |
| Na | 9 |
| Mo | 3.5 |
| U | 1.3 |
| Co | 2.0 |
| Ce | 1.8 |
| La | 0.69 |
| W | 0.2 |
| Sb | 0.07 |
| Th | 0.18 |
| Br | 0.11 |
| Sm | 0.08 |
| As | 0.06 |
| Sc | 0.02 |
| Au | 0.002 |

As in the case of the Al-foil targets, the results from processing hundreds microCi of Ra/Al-mesh discs targets indicated that the selective leaching of Ra and Ac from the Al mesh (developed for the Al disc target) can be also performed. Already during the dissolution of the target it is possible to separate most of the Al and impurities from the Ac.

A special advantage of the radium targets as described in DE 103 47 459 B3 and DE 10 2004 022 200 A1 is that they exhibit basically pure radium material in their radium containing coating. Hereby it is achieved that the targets are free of carriers or diluents, for example barium salts, which had to be added to the conventional radium targets of the prior art, in order to homogenize the radium-containing material. Due to the possibility to be able to work without such carrier materials as barium compounds, the chemical separation and purification of the created $^{225}$Ac becomes substantially more simple and the yields of irradiation are optimized, as competitive nuclear reactions, as for example those from barium nuclei, are not possible.

To summarize, however, despite the already optimized target systems as provided by Applicant's DE 103 47 459 B3 and DE 10 2004 022 200 A1, the final $^{225}$Ac-product still contains significant amounts of inorganic, radionuclide and organochemical impurities, which render the obtained $^{225}$Ac product unsuitable for direct medical or pharmaceutical application.

In other words, the achieved product cannot be used immediately to prepare a pharmaceutical grade $^{225}$Ac-product for the manufacture of the radiopharmaceutical agents described in the introductory part of the present specification for cancer therapy.

As a result, it is the object of the present invention to provide a purified and pharmaceutically acceptable $^{225}$Ac-containing radionuclide composition for further processing in the manufacture of $^{225}$Ac-containing therapeutic agents.

With respect to a method, the above object is independently achieved by the characterising features of claims 1, 2, and 3.

A pharmaceutically acceptable $^{225}$Ac-containing radionuclide composition in accordance with claim 21 also solves the above problem.

In particular, the present invention suggests a method for purification of $^{225}$Ac from irradiated $^{226}$Ra-targets provided on a support, comprising the following steps:

a) at least one leaching treatment of the $^{226}$Ra-targets for leaching essentially the entirety of $^{225}$Ac and $^{226}$Ra with nitric or hydrochloric acid under refluxing conditions;

b) removing HCl if the solvent in step b) is hydrochloric acid and redissolving the resulting material in nitric acid;

c) concentrating the $^{225}$Ac and $^{226}$Ra containing extracts;

d) separating $^{225}$Ac from $^{226}$Ra and other Ra-isotopes by means of at least one first extraction chromatography with a solid support material having a first extractant system coated thereon, comprising at least one compound in accordance with general formula I in at least one compound in accordance with general formula II,

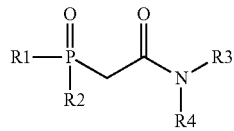

Formula I

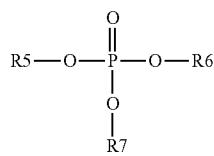

Formula II wherein in formula I:

R1, R2 independently is octyl, n-octyl, phenyl, or phenyl substituted with $C_1$ to $C_3$ alkyl;

R3, R4 independently is propyl, isopropyl, butyl, or isobutyl;

wherein in formula II:

R5, R6, and R7 independently is $C_2$-$C_5$ alkyl, in particular, butyl, or isobutyl;

e) eluting $^{225}$Ac which is retained on the solid support from the stationary phase with diluted nitric or hydrochloric acid, whereas $^{226}$Ra is passing through;

f) separating $^{225}$Ac from $^{210}$Po and $_{210}$Pb by means of at least one second extraction chromatography with a solid support material having a second extractant system coated thereon, comprising at least one compound in accordance with general formula III in at least one compound in accordance with general formula IV,

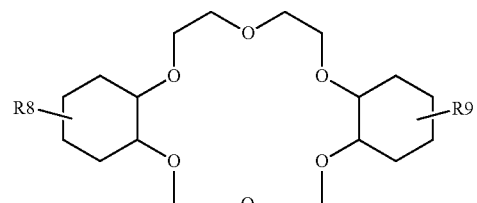

Formula III

R10—OH    Formula IV wherein in formula III:

R8 and R9 independently is H, $C_1$-$C_6$ alkyl, or t-butyl; and wherein in formula IV:

R10 is $C_4$ to $C_{12}$ alkyl;

g) using 2M HCl as mobile phase; and h) recovering $^{225}$Ac from the flow-through, whereas $^{210}$Po and $^{210}$Pb are retained on the solid support.

Alternatively, the method of the present invention for purification of $^{225}$Ac from irradiated $^{226}$Ra-targets provided on a support, comprises the following steps:

a) at least one leaching treatment of the $^{226}$Ra-targets for leaching essentially the entirety of $^{225}$Ac and $^{226}$Ra with nitric or hydrochloric acid under refluxing conditions;

b) removing HCl if the solvent in step b) is hydrochloric acid and redissolving the resulting material in nitric acid;

c) concentrating the $^{225}$Ac and $^{226}$Ra containing extracts;

d) separating $^{225}$Ac from $^{226}$Ra and other Ra-isotops by means of at least one first extraction chromatography with a solid support material having a first extractant system coated thereon, comprising at least one compound in accordance with general formula IA,

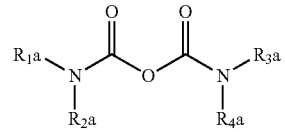

Formula IA wherein in formula IA:

R1a, R2a, R3a, R4a independently is octyl or 2-ethylhexyl;

eluting $^{225}$Ac which is retained on the solid support from the stationary phase with nitric acid within a concentration range of 0.3 M to 0.01 M or 1 M to 0.05 M hydrochloric acid, whereas $^{226}$Ra is passing through;

f) separating $^{225}$Ac from $^{210}$Po and $^{210}$Pb by means of at least one second extraction chromatography with a solid support material having a second extractant system coated thereon, comprising at least one compound in accordance with general formula III in at least one compound in accordance with general formula IV.

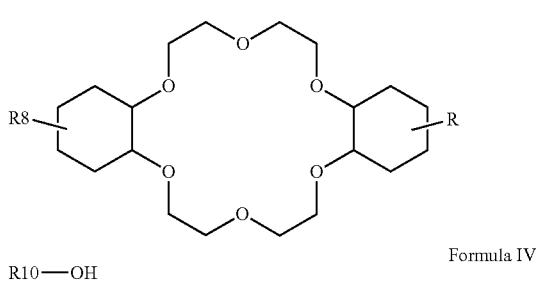

Formula III

R10—OH  Formula IV wherein in formula III:

R8 and R9 independently is H, $C_1$-$C_6$ alkyl, or t-butyl; and wherein in formula IV:

R10 is $C_4$ to $C_{12}$ alkyl;

g) using 2M HCl as mobile phase; and h) recovering $^{225}$Ac from the flow-through, whereas $^{210}$Po and $^{210}$Pb are retained on the solid support.

A further alternative method for purification of $^{225}$Ac from irradiated $^{226}$Ra-targets provided on a support, comprises the following steps:

a) at least one leaching treatment of the $^{226}$Ra-targets for leaching essentially the entirety of $^{225}$Ac and $^{226}$Ra with nitric or hydrochloric acid under refluxing conditions;

b) removing HCl if the solvent in step b) is hydrochloric acid and redissolving the resulting material in nitric acid;

c) concentrating the $^{225}$Ac and $^{226}$Ra containing extracts;

d) separating $^{225}$Ac from $^{226}$Ra and other Ra-isotops by means of at least one first extraction chromatography with a solid support material having a first extractant system coated thereon, comprising a compound in accordance with formula IB,

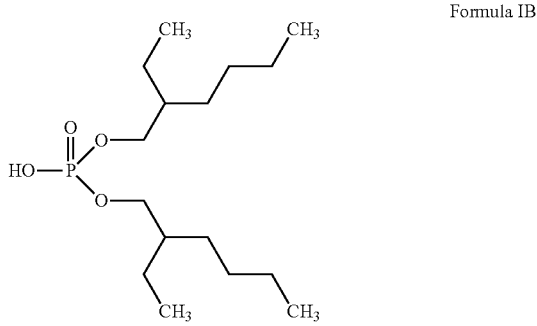 [SMILES: CCCCC(CC)COP(=O)(O)OCC(CC)CCCC]

Formula IB de) eluting $^{225}$Ac which is retained on the solid support from the stationary phase with nitric acid having a concentration lower than appr. 0.1 M and higher then appr. 0.02 M, whereas $^{226}$Ra is passing through;

f) separating $^{225}$Ac from $^{210}$Po and $^{210}$Pb by means of at least one second extraction chromatography with a solid support material having a second extractant system coated thereon, comprising at least one compound in accordance with general formula III in at least one compound in accordance with general formula IV,

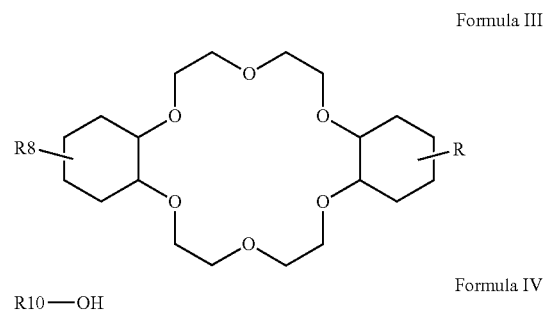

Formula III

R10—OH  Formula IV wherein in formula III;

R8 and R9 independently is H, $C_1$-$C_6$ alkyl, or t-butyl; and wherein in formula IV:

R10 is $C_4$ to $C_{12}$ alkyl;

g) using 2M HCl as mobile phase; and h) recovering $^{225}$Ac from the flow-through, whereas $^{210}$Po and $^{210}$Pb are retained on the solid support.

In a preferred method according to the invention, said nitric acid in step a) has a concentration range of appr. 0.001 M to 2 M, preferably appr. 0.1 M and said hydrochloric acid has a concentration range of 0.001 M to 2 M, and/or said acids are used at elevated temperatures, in particular, from appr. 30 to 90° C.

Preferably, extracts from the leaching treatment are pooled and used for further processing.

In concentration step c), typically, a final concentration of 1.5 M to 10 M of nitric acid is achieved.

In a preferred embodiment of the invention, the first extractant system is octyl(phenyl)-N,N-diisobutylcarbamoylphosphine oxide [CMPO] in tributyl phosphate [TBP].

The second extractant system can be very efficiently a crown ether in accordance with formula V:

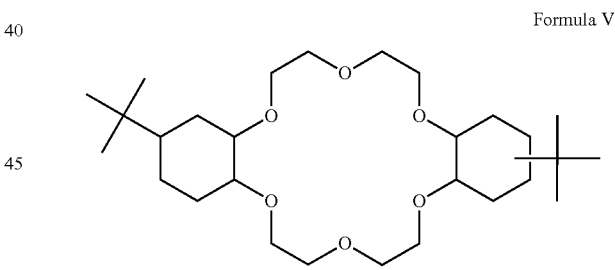

Formula V

Preferably, the crown ether of Formula V is used in 1-octanol.

In a particularly preferred method of the invention, the second extractant system is 4,4'-bis(t-butylcyclohexano)-18-crown-6 in 1-octanol.

An alternative second extractant system is 4,5'-bis(t-butylcyclohexano)-18-crown-6 in 1-octanol.

In order to improve the final purification method, the first extraction chromatography of step d) can be repeated several times, in order to remove trace amounts of Ra-isotopes, depending on the desired purity of the $^{225}$Ac.

In an analogues manner, the second extraction chromatography of step f) can be repeated several times, depending on the desired purity of the $^{225}$Ac.

In a case of need, the first and the second extraction chromatography steps can be repeated several times for higher purification grades.

In the method according to the present invention, it is preferred to remove Radon which is contained in the Al-support and/or in the converted products from the $^{225}$Ac products and the Al-support during the leaching process by means of suitable traps.

Radon removing can be achieved for example easily by guiding Rn into a first alkaline trap to, neutralize acidic vapors, into a subsequent silica trap to absorb water, and into a final activated coal trap, wherein the activated coal trap is optionally cooled.

Due to its value and hazardous potential, not converted $^{226}$Ra starting material is recovered from the flow-through of step e).

$^{210}$Po and $^{210}$Pb impurities are eluted from the solid support of the second extraction chromatography in step h) by means of concentrated nitric acid or hydrochloric acid.

In the present method of the invention, each purification step and/or fraction is preferably checked by means of α- and/or γ-spectroscopy.

Respective fractions containing:
a. $^{225}$Ac; or
b. Ra-isotopes; or
c. $^{210}$Po; and
d. $^{210}$Pb are evaporated to wet or dry residues and redissolved, if necessary.

For removing organochemical impurities, it is preferred to pass the prepurified $^{225}$Ac solutions through a resin filter which contains a non-ionic acrylic ester polymer.

The final product as obtainable with the method of the present invention is a pharmaceutically acceptable $^{225}$Ac-containing radionuclide composition which can be used to prepare $^{225}$Ac-bearing radiopharmaceuticals as disclosed in the introductory part of the present specification.

The present invention further comprises all combinations of all disclosed single features together, independent from their AND- or OR-linkage.

Further advantages and features can be seen from the description of examples and the drawings.

FIG. 1 shows a general scheme for the extraction of $^{225}$Ac from $^{226}$Ra/Al irradiated targets;

FIG. 2a. shows a γ-spectrum of the $^{226}$Ra-fraction after first Ra/Ac separation with the RE Resin;

FIG. 2b. shows a γ-spectrum of the purified $^{226}$Ac-fraction:

FIG. 3a. shows a γ-spectrum of $^{225}$Ac prior to Po and Pb purification; and

FIG. 3b. shows a γ-spectrum of $^{225}$Ac after Pa and Pb purification.

1. Preparation of Purified $^{226}$Ra Material for Target Preparation

A Ra batch sealed $^{226}$Ra source is pre-checked by γ-spectrometry, ampoule is broken. The Ra salts or compounds are dissolved and the solution is separated from glass by filtration. The filter and glass particles are leached out with 0.5 M HNO$_3$ and pooled with $^{226}$Ra-containing liquid. This solution is subjected to an at least one extraction chromatography step, which results in a purified Ra fraction.

The latter fraction is used—after a further concentration step—for preparing the $^{226}$Ra targets.

Further details of $^{226}$Ra purification for cyclotron target preparation for $^{225}$Ac manufacture are described in the not prepublished DE 102005043012, filed on 9 Sep. 2005. The disclosure of this patent application is herewith incorporated by reference in its entirety.

2. Preparation of a $^{226}$Ra Target by Electrodeposition by Means of a Fixed Aluminium Disc as Cathode The present invention will be illustrated by way of an example of a target preparation by means of an electrodeposition according to DE 103 47 459 B3, "Radium-Target sowie Verfahren zu seiner Herstellung".

The person having average skill in the art will understand that the invention also works in targets prepared by the evaporation method in accordance with DE 10 2004 022 200 A1 "Method for producing $^{226}$Ra targets by the droplet-evaporation methods for irradiation in the cyclotron".

For the preparation of a $^{226}$Ra target, aluminium discs with a thickness of 0.015 mm and a diameter of about 5 cm with a minimal 99% purity of the aluminium are punched out and fixed on a stainless steel support. The support facilitates the handling of the aluminium foils and is removed after the electrodeposition itself, before the positioning of the radium-coated foil in the target itself.

For the electrodeposition on the aluminium foil, a solution of a radium-226-nitrate is used, whereby in particular 226-radium chloride or 226-radium carbonate are absorbed beforehand for the transformation into the corresponding nitrate in about 0.05 M HNO$_3$.

Subsequently, the stainless steel support, on which the aluminium foil is fixed, is weighted and the net weight of the aluminium foil is determined.

150 ml (for electrodeposition on aluminium foils with a diameter of up to 15 cm) or 10 to 11 ml isopropanol are added into an electrodeposition cell (for aluminium foil discs with a diameter up to 2 cm).

Then the required amount of radium-226 solution is filled into the electrolytic cell and 1-2 ml 0.05 M HNO$_3$ are added. The total volume of the radium solution and 0.05 M HNO$_3$ should not exceed about 2 ml, if aluminium foil discs with a diameter of up to 2 cm are used, and 20 ml at the most, if aluminium foil discs with a diameter of up to 15 cm are used. When high radium concentrations are used, a white precipitates may be formed. If this happens, 0.05 MHNO$_3$ is further added until the precipitation has dissolved. The pH value of the depositing plating solution should preferably be between 4 and 5.

For the electrodeposition of $^{226}$Ra containing material out of the plating solution the electric current is adjusted to about 60 mA and a voltage of about 200V is applied, monitored for a few minutes and, if necessary, readjusted.

After the electrodeposition of the $^{226}$Ra solution has been completed, the plating solution is poured out, the support is rinsed with 2 to 3 ml isopropanol and the cell is disassembled and the aluminium foil is additionally rinsed with about 1 to 2 ml isopropanol.

Afterwards, the support with the $^{226}$Ra coated aluminium foil arranged on it is dried under an infrared lamp until the weight remains constant, in order to render the radium-containing coating anhydrous.

Afterwards, the stainless steel support with the fixed, coated aluminium foil is weighted and the net mass of the coated aluminium foil is determined. Then the yield is determined from the weighted mass of the $^{226}$Ra containing layer.

An alternative way to monitor the yield of the electrodeposition—instead of weighing—is to measure the γ-activity of $^{226}$Ra by means of a high resolution γ-spectrometer.

Subsequently, the stainless steel support and the aluminium foil are separated from each other.

The dry aluminium fail coated with radium compounds is carefully covered with a new aluminium foil and the edges of the aluminium foil with which the Aluminium foil carrying the active layer is fixed are cut off, in order to minimize the amount of aluminium in the target itself.

For the use as radium target in the proton beam of a cyclotron, a pile of the of the circular disc shaped aluminium foils prepared according to present examples, which are coated with radium-containing material in a ring shaped manner, are piled in a so called target cup.

For the production of a folded radium target, one or more aluminium foils, in the case of this example, coated on one whole surface with $^{226}$Ra are covered in a way with another aluminium foil that the radium containing film is covered entirely. Then, the aluminium foil is folded several times until stripes of about 2 mm are obtained. The folded aluminium foil, which contains the layers of radium-containing material, in particular radium oxides, is then placed into the target for proton irradiation in the cyclotron or in the linear accelerator.

With the above methods according to DE 103 47 459 B3 and DE 10 2004 022 200 A1, it is possible to obtain highly potent $^{226}$Ra targets on aluminium foil of a different thickness with different $^{226}$Ra-amounts.

This method assures in particular to deposit s that are highly homogenous on the aluminium-$^{226}$Ra target. This is particularly important for the irradiation of the target in the cyclotron, as the atomic nuclei of radium are thereby exposed homogenously to the proton flux.

The use of aluminium as substrate for $^{226}$Ra offers various advantages for the irradiation in a cyclotron and the subsequent radiochemical processing of the irradiated target. The advantages of the aluminium lie in the nuclear physical and chemical properties of the aluminium:

Nuclear properties: Aluminium has just one single stable isotope. The activation products formed from the aluminium are very short-lived. The formation of only short lived radionuclides on aluminium facilitates the radiochemical purification of Ac-225 and reduces the coaling time of the target after irradiation. As the loss of energy of protons in aluminium is very low, it is possible to use several thin films of aluminium without substantial reduction of the proton energy.

Physical properties: Aluminium is a light metal with good thermal and electrical conductivity. It is easy to handle and can be adapted easily to the required geometry.

Chemical properties: Aluminum can easily be dissolved in mineral acids and it can be easily separated from the resulting Actinium. Aluminum foils are available with a high degree of chemical purity and at reasonable prices.

The deposition of $^{226}$Ra, e.g. as oxide or peroxide, allows to obtain a layer with a high content of radium, in particular about 70% of the deposited material per cm$^2$. The electrodeposition yield is high.

In practice it has turned out that about 4 to 5 g/cm$^2$ $^{226}$Ra with goad adhesive properties can be deposited on the aluminum foil.

3. Purification of $^{225}$Ac Produced by $^{226}$Ra Cyclotron Irradiation with Protons A. Selective Leaching of Ac and Ra from Irradiated Ra/Al Targets Prepared by the Electrodeposition Technique After the irradiation at the cyclotron, the target containing Ac and Ra is transferred to a shielded glove box and positioned in the disassembling and dissolution position. For leaching Ra and Ac from the irradiated Al discs or rings, a refluxing/distillation arrangement is used. This set up enables the condensation of hot water and acids vapours and their continuous reflux into the dissolution vessel and the collection of condensates when this is required. Using this arrangement any Rn which could be still present in the irradiated Al discs can be trapped in a series of traps. The traps are assembled in the following sequence: a NaOH bath to neutralize acid vapors, a silicagel trap to absorb water vapours and finally an activated cooled-coal trap to capture Rn.

The arrangement used for leaching Ra and Ac from irradiated disc targets is a Refluxing/Destillation arrangement. Typically, the discs or rings are inserted in the flask and they are treated first with 30 ml hot 0.1-0.2 M HNO$_3$ and then with 30 ml boiling 2M HNO$_3$ or HCl. The leaching processes are repeated two-three times to wash out any remaining activities of Ra or Ac attached to the discs or to the walls of the glass vessel. The leaching solutions are first subjected to gamma-spectrometry and then combined if required.

As a result of the leaching process at least two fractions are obtained: the first one contained the Ac, the Ra and part of the activation products (0.1-0.2 M HNO$_3$) and the second contained most of the matrix (Al) and part of the activation products (2M HNO$_3$ or concentrated HCl). The 0.1-0.2 M HNO$_3$ fraction is taken for the Ac extraction process. This solution is converted to 2M HNO$_3$, during this conversion any particles which can be suspended in solution should be dissolved. The volume of this fraction is generally set to 30 ml.

The results indicate that more than 99% of Ac and Ra is contained in this fraction. Only trace amounts of Ac and Ra are found in the second leaching solution of 2M HNO$_3$ which contains most of the Al from the Al discs. The activation products are found almost equally distributed between these two leaching fractions. This procedure facilitates the purification and recycling of Ra because both Ac and Ra are extracted from the foil or mesh without the total dissolution of the Al. In addition, the lower beta and gamma activity associated with activation products in the Ac/Ra leaching solution reduces the risk of radiation damage of the used resins, in particular RE resin.

B. Selective Leaching of Ac and Ra from Irradiated Ra Targets Prepared by the Droplet-Evaporation Technique The Ra and Ac are removed from the irradiated Al cup by washing it with a 0.1 M HNO$_3$ solution in an ultrasonic bath. After irradiation at the cyclotron and target disassembling in a shielded glove box; the Al target-cup which carries high radiation dose is transferred and placed into a 250 ml glass beaker (chosen for this specific target cup). This beaker is inserted in an ultrasonic bath. Once the target is inside the beaker or container, 100 mL 0.1M HNO$_3$ are added into the Al-cup. This volume of 100 ml was selected to completely immerse the target into the leaching solution (the volume depends on the geometry and size of the target cup). The ultrasonic bath is then activated and the temperature of the water bath is kept at approximately 80 C during the process. The leaching process with the ultrasonic bath is conducted two times for short time (not more than 20-30 minutes). AN liquid fractions containing the Ra and Ac are combined in a glass beaker and evaporated to wet residues. Experiments with Ba nitrate has previously indicated that Ba at these conditions (setup, leaching volume, duration of US bath) is completely removed. The experiments with Ba also demonstrate that some particulate material associated with Al oxide is released from the target cup. Consequently before starting the separation process, this particulate fraction has to be dissolved either in hot 2M $HNO_3$ or, if necessary, in 6M HCl and then converted to 2M $HNO_3$. This solution is taken for the radiochemical separation. The recovery of Ra and Ac from the irradiated target by using this technique is always higher that 90%.

Studies are being currently carried out to minimize the volume of 0.1M $HNO_3$ solution needed to quantitatively recover the Ra and Ac from the target cup with a high chemical purity. These studies are conducted using also a new target design. Using this target we will be able to leach out the Ac and Re from the target cup without the need of disassembling it. The chemical purity of the leaching solution will define the complexity of the Ra recycling and purification process and therefore, it is important to obtain a chemical pure Ra solution already at this stage.

C. Separation of Ac from Ra and Most of the Activation Products by Extraction Chromatography using the RE Resin as a First Extractant System The Ac/Ra separation is based on the use of the extraction chromatography resin RE Resin (EiChrom). In the RE resin, the stationary phase consist of octyl(phenyl)-N,N-diisobutylcarbamoylphosphine oxide in tributylphosphate. This extractant has the property to extract trivalent actinides and lanthanides from nitric acid solutions (e.g. 2M $HNO_3$). The Ac can be eluted from the stationary phase by washing the column with diluted solutions of nitric or hydrochloric acid (e.g. 0.05M $HNO_3$).

Background Information

The extraction of trivalent actinides especially transplutonium elements with bidentate organophosphorus compounds was extensively studied in the USA and the former USSR. In the USA, for example Horwitz et al. (1984, 1993) studied the extraction of Am and other elements with a great number of carbamoylphosphonates and carbamoylphosphine oxides. It was established that both kinds of extractants form trisolvates with lanthanides and trivalent actinides. The high extraction coefficient from nitric acid medium was explained by the bidentate coordination and cycle chromatography versions of the extraction system CMPO/TBP (e.g. TRU resin or RE resin, distributed by EICHROM). On both resins the tetravalent actinides show high retention from nitric acid solutions, having for example capacity factors (CF) in the range of $10^4$-$10^6$ from 2-3 M $HNO_3$ for the TRU Resin. In the same range of concentration, the CFs for lanthanides is in the order of 100 on the TRU Resin and between 100-200 on the RE Resin. For the RE, the CFs are higher for all relevant elements. The low retention of trivalent actinides from HCl and from diluted nitric acid solutions is the basis for their selective elution. According to Horwitz (1993); Ca, Fe (II) and commonly occurring polyatomic anions do not show significant effect on the Am retention from $HNO_3$. Based on these properties, the TRU Resin has been applied for the separation of Am from Sr, Ca and Ba in environmental samples (e.g. Burnett et al.; 1995; Moreno et al., 1997 and 1998). Burnett et al. (1995) applied the RE Resin in the combined determination of very small quantities of both $^{226}$Ra and $^{228}$Ra in environmental samples.

In an entirely novel approach, in the present invention, the inventors have used the RE Resin for the separation of Ac from $^{226}$Ra, Al and from most of the activation products produced at the cyclotron by selectively extracting the Ac from 2 M $HNO_3$. Ac is eluted from the stationary phase using 0.03-0.05 M $HNO_3$.

Separation of Ac from Ra, Al and Activation Products after the Irradiation of Ra/Al Targets at the Cyclotron FIG. 1 shows the flow chart of processes used for the extraction of Ac from irradiated targets. The size of the columns used (8 ml-bed volume) is chosen to maximize the retention of Ac on the RE resin from a large volume of loading solution and consequently to reduce the breakthrough of Ac in the Ra fraction. Assuming that a maximum of 0.5 g Ra and 0.5 g (extreme conditions) of Al can be present in the leaching/loading 2 M $HNO_3$ solution, a total volume of up to 70-80 ml is needed for the total dissolution of Ra and Al. The results from experiments conducted with synthetic solutions and also with irradiated targets (ma of Ra and hundreds μCi of $^{225}$Ac) indicate that under similar conditions, most of the Ra can be removed by washing the column with approximately 50 ml 2 M $HNO_3$ without a significant breakthrough of Ac. Meanwhile, most of the Ac can be eluted with 50 ml 0.05 M $HNO_3$. The typical decontamination factor $D_f$(Ac/Ra) is found to be in the order of $10^4$ (one stage).

D. Purification of the Ac

D1. From Tracer Quantities of Ra by using a Repeated Extraction Chromatography Column with the RE Resin After the separation of the bulk of Ra, Al and activation products; $^{210}$Po (FIG. 3a) and some small quantities of Ra and isotopes of transition elements still remain in the Ac fraction. Therefore, a second separation of Ac from these remaining impurities is necessary. As shown in FIG. 1, the purification process consists of two stages: the first is a repetition of the Ac/Ra separation using the RE resin to provide an additional decontamination of Ac from Ra. The experiments have shown that the total decontamination factor Ac/Ra is approximately $10^6$-$10^7$ by repeating twice the Ac/Ra separation with the RE resin under the described conditions.

A further purification step enables the Ac/Po, Ac/Pb and Ac/Rn separation using a second extractant system, the Sr Resin (Eichrom) and this process is described below in section D2.

D2. From Po and Pb Isotopes by using the Sr Resin as a Second Extractant System

Background Information

In the Sr Resin of the present example, the extractant in the stationary phase is a crown ether: 4,4'(5')-bis(t-butylcyclohexaneno)-18-crown-6 in 1-octanol, Horwitz (1991, 1992) proposed this crown ether in 1-octanol to selectively extract Sr from concentrated nitric acid solutions. The extraction chromatography system is commercially available as Sr Resin (Eichrom) and has been applied to the determination of very low activities of $^{210}$Pb in environmental samples (Vajda et al,; 1995). Indeed, this resin has been also frequently used for the separation and purification of $^{90}$Sr from Ca, Mg and Ba in the radiochemical analysis of environmental samples (Vajda N. et al., 1992; Moreno et al, 1997 and 1998). In the present invention, the inventors have used the Sr Resin as second extractant system to purify Ac from Po, Pb and also Rn in 2 M HCl solutions: while Pb and Po are retained by the stationary phase from 2 M HCl, Ac passes through.

Separation of Ac from Po and Pb in the Purification Scheme

The presence of Po in the Ac (FIG. 3a) is observed on the alpha spectrum obtained from the Ac after the RE Resin separation. The presence of both Pb and Po in the Ac can be confirmed by measuring the gross alpha beta activity of aliquots taken from the Ac fraction. Without performing the purification with the Sr Resin, this parameter (gross alpha and beta activities) is much higher that the expected gross activity associated with the Ac and its decay products. Experiments carried out in dynamic conditions demonstrate that while Ac passed through the column, both Po and Pb were retained from 2M HCl acid. The 2M HCl fraction (loading and washing 2M HCl solutions) contained the Ac (FIG. 3b) while Po and Pb were retained by the stationary phase.

E. Final Purification and Pre-Concentration of the Purified Ac Fraction

Before proceeding with the final preconcentration step, the Ac fraction in 2M HCl acid from the Sr Resin is subject to quality control. At this stage, the radioisotopic purity is generally very high and it depends mainly on the presence of the short living $^{135}$La. Consequently the purity quickly increases within a few days after the end of production to more than 99.7%. The activity ratio $^{226}$Ra/$^{225}$Ac (and also the activity ratio in relation to other long-lived isotopes) is checked and this ratio was usually below $5.10^{-4}$ in the Ac fraction.

If the conditions for radioisotopic purity were not fulfilled, then a further purification of Ac from Ra and other relevant components is required. For this purpose, the Ac fraction obtained after concentration of the 2 M HCl solution is subject to a fast purification from Ra using a 2 ml-bed volume column with the RE resin. Usually, there is also a need to purify the Ac from soluble or dispersed organic materials. To separate the organic material, the solution is passed through a pre-filter 2 ml-bed volume resin (Eichrom) which contains a non-ionic acrylic ester polymer. The results indicate that the content of soluble organics is decreased in one order of magnitude and all the Ac can be filtered through this resin without retention.

The results from the manual reprocessing of irradiated Ra/Al targets show that the recovery of Ac and Ra (excluding the recycling and further purification) are higher than 98% and 96% respectively. For processes conducted with 2- to 3 mg of Ra and hundreds μCi of $^{225}$Ac and using almost fully automated processes, the recovery factor of Ra is slightly lower but generally higher than 90-92%. This factor is intended to be increased by optimizing parameters associated with the automatic processes (e.g. liquid transfer, dead volumes, etc).

F. Radioisotopic Impurities Measured by γ-Spectrometry

The radioisotopic purity and the chemical purity of the Ac depend on the applied radiochemically procedures and also on the purity of the materials (mesh carrier, TC, etc) arid reagents (Ra solution, acids, etc). Particularly important is to minimize the content of Sr and Ba which lead to the production of radioisotopes of Y and La respectively that behave similarly to Ac during the separation process.

As already mentioned in the introduction, several radioisotopes are produced as a result of nuclear reactions type (p,n) or (p,2n) on main impurities like Ba, Fe, Zn, Sr, Pt, V, Ti, Cr and Cu which are present in the Al carrier (foil, mesh) and/or in the Ra deposit. As an example, the γ-spectrum of a Ra fraction is shown in FIG. 2a. The radionuclides of major contribution to the total gamma activity excluding $^{226}$Ra and daughters were typically the following: $^{135}$La, $^{55}$CO, $^{56}$CO, $^{67}$Ga, $^{57}$Ni, $^{135m}$Ba, $^{133m}$Ba, $^{131}$Ba, $^{129}$Cs, $^{51}$Cr, $^{48}$V, $^{52}$Mn, $^{54}$Mn, $^{65}$Zn. Except for RE isotopes, most of these radionuclides are separated from the Ac. The typical radioisotopic purity of the purified Ac fraction is higher than 99.8% (see Table 2). The γ-spectrometry measurements of the purified Ac fraction (FIG. 3b) showed the presence of small quantities of rare earth radioisotopes, namely $^{87}$Y, $^{88}$Y, $^{139}$Ce. Small quantities of $^{194}$Au were some times observed (Pt anode) when the target was prepared by electrodeposition (Pt anode).

Radioisotopic Impurities Measured by γ-Spectrometry

The γ-spectrometry results after radiochemical separation of Ra in the aliquot sample indicate that the combined decontamination factor of $^{225}$Ac in relation to $^{226}$Ra ($D_f$) is $10^6$-$10^7$. This factor can be significantly improved by optimizing relevant parameters associated with the purification process.

FIG. 3b shows the spectrum of the purified Ac extracted from an irradiated target. The spectrum clearly shows the peaks of $^{225}$Ac and decay products. No impurities of $^{210}$Po were observed which indicate that decontamination of $^{225}$Ac from $^{210}$Po is also very high by applying the described radiochemical scheme (see FIG. 3a).

The content of impurities will decrease by increasing a proper selection of high purity reagents and materials (e.g. Al foils/mesh of better purity). In addition, when Bi is eluted from the Ac/Bi generator, the rare earth radioisotopes Ce, Ln, Y, and any $^{226}$Ra will remain on the stationary phase along with Ac (Ac/Bi generator) thus providing additional purification of $^{213}$Bi.

TABLE 2

Radioisotopic impurities measured in a purified Ac fraction from irradiated target (electrodeposition).

| Radionuclide | Activity [Bq] | Activity ratio $a_i/a_{Ac}$ [b] | Activity ratio $a_{i,t}/a_{Ac}$ [c] | Radioisotopic purity [%] |
|---|---|---|---|---|
| $^{88}$Y | 4.66 | $1.57 \times 10^{-4}$ | $4.1 \times 10^{-4}$ | 99.96 |
| $^{139}$Ce | 7.82 | $2.64 \times 10^{-4}$ | | |
| $^{226}$Ra | 0.4[a] | $1.3 \times 10^{-5}$ | | |
| $^{209}$Tl | 562 | | | |
| $^{221}$Fr | $2.93 \times 10^4$ | | | |
| $^{213}$Bi | $2.91 \times 10^4$ | | | |
| $^{225}$Ac | $2.96 \times 10^4$ | | | |

Except for $^{226}$Ra, all results were obtained by high resolution gamma-spectrometry
[a] α-spectrometry after radiochemical separation of Ra (two independent analyses)
[b] $a_i/a_{Ac}$ impurity/actinium activity ratio
[c] $a_{i,t}/a_{Ac}$ ratio of the activity of all impurities to the activity of $^{225}$Ac
$^{55}$Co, $^{56}$Co, $^{57}$Co, $^{58}$Co, $^{67}$Ga, $^{194}$Au, $^{206}$Bi, $^{205}$Bi, $^{51}$Cr, $^{87}$Y, $^{48}$V, $^{54}$Mn, $^{65}$Zn, $^{226}$Ra, $^{214}$Pb and $^{214}$Bi were not detectable by γ-spectrometry.

Chemical Impurities Measured in the Purified Ac Fraction

The typical content of total inorganic impurities in the Ac purified fraction is generally below 100 μg. The following elements have been detected and quantified in the Ac fraction: Al, Ba, Ca, Cr, Cu, K, La, Mg, Mn, Na, P, Rb, Si, Sr, Ti, Zr, Zn and Zr.

Thus, with the method according to the invention a pharmaceutically acceptable $^{225}$Ac preparation can be obtained, and the $^{226}$Ac can be used for the preparation of nuclear drugs for treatment of cancer as described in the introductory part of the present specification.

The invention claimed is:

1. A method for purification of $^{225}$Ac from irradiated $^{226}$Ra-targets provided on a support, comprising the following steps:
 a) leaching $^{225}$Ac and $^{226}$Ra from one or more $^{226}$Ra-targets with a nitric acid solvent in a refluxing/distillation arrangement to generate one or more $^{225}$Ac and $^{226}$Ra containing extracts, wherein said nitric acid solvent has a concentration range of about 0.001 M to about 2 M;

b) concentrating the $^{225}$Ac and $^{226}$Ra containing extracts, wherein the concentrating results in a $^{225}$Ac and $^{226}$Ra containing extract having a concentration of about 1.5 M to about 10 M of $HNO_3$;

c) separating $^{225}$Ac from $^{226}$Ra and other Ra isotopes by means of at least one first extraction chromatography with a solid support material having a first extractant system coated thereon, comprising at least one compound in accordance with general formula IA,

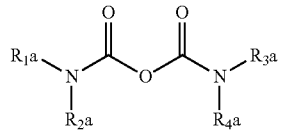

Formula IA wherein in formula IA:
R1a, R2a, R3a, R4a independently is octyl or 2-ethylhexyl;

d) allowing the $^{226}$Ra to flow through and then eluting $^{225}$Ac retained on the solid support with nitric acid having a concentration between about 0.01M and about 0.3M or with hydrochloric acid having a concentration between about 0.05M and about 1M;

e) separating $^{225}$Ac from $^{210}$Po and $^{210}$Pb by means of at least one second extraction chromatography with a solid support material having a second extractant system coated thereon, comprising at least one compound in accordance with general formula III in at least one compound in accordance with general formula IV, Formula III Formula IV wherein in formula III:
R8 and R9 independently is H, $C_1$-$C_6$ alkyl, or t-butyl;
and
wherein in formula IV:
R10 is $C_4$ to $C_{12}$ alkyl;

f) using 2M HCl as mobile phase; and g) recovering $^{225}$Ac as a flow-through separately from $^{210}$Po and $^{210}$Pb, which are retained on the solid support.

2. A method for purification of $^{225}$Ac from irradiated $^{226}$Ra-targets provided on a support, comprising the following steps:

a) leaching $^{225}$Ac and $^{226}$Ra from one or more $^{226}$Ra-targets with a nitric acid solvent in a refluxing/distillation arrangement to generate one or more $^{225}$Ac and $^{226}$Ra containing extracts, wherein said nitric acid solvent has a concentration range of about 0.001 M to about 2 M;

b) concentrating the $^{225}$Ac and $^{226}$Ra containing extracts, wherein the concentrating results in a $^{225}$Ac and $^{226}$Ra containing extract having a concentration of about 1.5 M to about 10 M of $HNO_3$;

c) separating $^{225}$Ac from $^{226}$Ra and other Ra isotopes by means of at least one first extraction chromatography with a solid support material having a first extractant system coated thereon, comprising at least one compound in accordance with general formula IB,

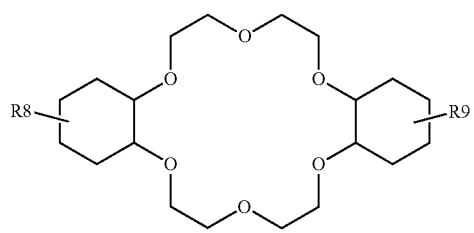

Formula IB d) allowing the $^{226}$Ra to flow through and then eluting $^{225}$Ac retained on the solid support with nitric acid having a concentration between about 0.02 M and about 0.1 M;

e) separating $^{225}$Ac from $^{210}$Po and $^{210}$Pb by means of at least one second extraction chromatography with a solid support material having a second extractant system coated thereon, comprising at least one compound in accordance with general formula III in at least one compound in accordance with general formula IV, Formula III Formula IV wherein in formula III:
R8 and R9 independently is H, $C_1$-$C_6$ alkyl, or t-butyl;
and
wherein in formula IV:
R10 is $C_4$ to $C_{12}$ alkyl;

f) using 2M HCl as mobile phase; and g) recovering $^{225}$Ac as a flow-through separately from $^{210}$Po and $^{210}$Pb which are retained on the solid support.

3. The method of any one of claims 1 to 2, wherein the support is a metal, and is selected from the group consisting of Aluminum or Aluminum alloys, passivated Aluminum, anodized Aluminum, coated Aluminum, Aluminum coated with an element of a Platinum group, precious metals, elements from a Platinum group; and mixtures thereof.

4. The method of any one of claims 1 to 2, wherein the second extractant system is a crown ether in accordance with formula V:

Formula V

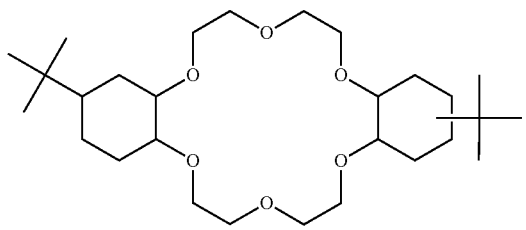

in 1-octanol.

5. The method of any one of claims 1 to 2, wherein the second extractant system is 4,4'-bis(t-butylcyclohexano)-18-crown-6 in 1-octanol.

6. The method of any one of claims 1 to 2, wherein the second extractant system is 4,5'-bis(t-butylcyclohexano)-18-crown-6 in 1-octanol.

7. The method of any one of claims 1 to 2, wherein the first extraction chromatography of step c) is repeated one or more times.

8. The method of any one of claims 1 to 2, wherein the second extraction chromatography of step e) is repeated one or more times.

9. The method of any one of claims 1 to 2, further comprising removing Rn from the support or the $^{225}$Ac and $^{226}$Ra containing extract during step a).

10. The method of claim 9, wherein the Rn is removed by means of a first alkaline trap to neutralize acidic vapours, a subsequent silica trap to absorb water, and a final activated coal trap.

11. The method of any one of claims 1 to 2, further comprising a step of recovering a $^{226}$Ra flow-through of step d).

12. The method of any one of claims 1 to 2, further comprising a step of eluting $^{210}$Po from the solid support of the second extraction chromatography in step g) by means of concentrated nitric acid or concentrated hydrochloric acid.

13. The method of any one of claims 1 to 2, wherein a fraction of a purification step is examined by means of α- and/or γ-spectroscopy.

14. The method of any one of claims 1 to 2, wherein a fraction of a purification step containing any one of:
  a) $^{225}$Ac;
  b) Ra-isotopes;
  c) $^{210}$Po; and
  d) $^{210}$Pb
is subjected to an evaporation step.

15. The method of any one of claims 1 to 2, further comprising a step of removing one or more organic impurities from a fraction of a purification step.

16. The method of any one of claims 1 to 2, wherein the nitric acid solvent of step a) has a concentration of about 0.1M.

17. The method of any one of claims 1 to 2, wherein the nitric acid solvent of step a) is used at a temperature of about 30 to 90° C.

18. The method of claim 10, wherein the activated coal trap is cooled.

19. The method of any one of claims 1 to 2, further comprising a step of eluting $^{210}$Pb from the solid support of the second extraction chromatography in step g) by means of concentrated hydrochloric acid or EDTA.

20. The method of claim 14, wherein the fraction is evaporated to a wet or a dry residue.

21. The method of claim 14, wherein the fraction is redissolved.

22. The method of claim 15, wherein the step of removing one or more organic impurities from a fraction of a purification step is performed by passing the fraction through a resin comprising a non-ionic acrylic ester polymer.

* * * * *

UNITED STATES PATENT AND TRADEMARK OFFICE
CERTIFICATE OF CORRECTION

PATENT NO. : 9,790,573 B2
APPLICATION NO. : 15/359053
DATED : October 17, 2017
INVENTOR(S) : Josue Manuel Moreno Bermudez et al.

Page 1 of 1

It is certified that error appears in the above-identified patent and that said Letters Patent is hereby corrected as shown below:

On the Title Page

The City name for Inventor #2 should read:
(72) Inventors: Andreas Turler, Ostermundigen (CH)

Item (57) should read:
(57) Abstract: The present invention describes a method for purification of $^{225}$Ac from irradiated $^{226}$Ra-targets provided on a support, comprising a leaching treatment of the $^{226}$Ra-targets for leaching essentially the entirety of $^{225}$Ac and $^{226}$Ra with nitric or hydrochloric acid, followed by a first extraction chromatography for separating $^{225}$Ac from $^{226}$Ra and other Ra-isotopes and a second extraction chromatography for separating $^{225}$Ac from $^{210}$Po and $^{210}$Pb. The finally purified $^{225}$Ac can be used to prepare compositions useful for pharmaceutical purposes.

Signed and Sealed this
Eighth Day of May, 2018

Andrei Iancu
*Director of the United States Patent and Trademark Office*